(12) United States Patent
Jiang et al.

(10) Patent No.: US 7,582,868 B2
(45) Date of Patent: Sep. 1, 2009

(54) METHOD OF NANO THIN FILM THICKNESS MEASUREMENT BY AUGER ELECTRON SPECTROSCOPY

(75) Inventors: Zhi Cheng Jiang, Dongguan (CN); Shan Dan Li, Dongguan (CN); Yuen Kwan Kam, Dongguan (CN); Yi Wei Liu, Dongguan (CN)

(73) Assignee: SAE Magnetics (H.K.) Ltd., Shatin, N.T. (HK)

( * ) Notice: Subject to any disclaimer, the term of this patent is extended or adjusted under 35 U.S.C. 154(b) by 340 days.

(21) Appl. No.: 11/192,199

(22) Filed: Jul. 27, 2005

(65) Prior Publication Data

US 2006/0138326 A1    Jun. 29, 2006

(30) Foreign Application Priority Data

Dec. 27, 2004   (WO) .............. PCT/CN2004/001529

(51) Int. Cl.
*G01N 23/00*  (2006.01)
(52) U.S. Cl. ........................................ 250/307; 250/306
(58) Field of Classification Search ....... 250/306–443.1
See application file for complete search history.

(56) References Cited

U.S. PATENT DOCUMENTS

| | | | | |
|---|---|---|---|---|
| 3,881,108 A | * | 4/1975 | Kondo et al. .................. | 850/43 |
| 5,714,757 A | * | 2/1998 | Itabashi et al. ................ | 850/63 |
| 6,215,631 B1 | * | 4/2001 | Fujikata et al. ........ | 360/324.11 |
| 6,310,343 B1 | * | 10/2001 | Koyama et al. ............. | 250/310 |
| 6,399,944 B1 | * | 6/2002 | Vasilyev et al. ............. | 250/310 |
| 6,906,863 B2 | * | 6/2005 | Yoshida et al. ............. | 359/584 |
| 2002/0109088 A1 | * | 8/2002 | Nara et al. ................... | 250/306 |
| 2004/0011957 A1 | * | 1/2004 | Yoshiki et al. .............. | 250/307 |
| 2004/0238886 A1 | * | 12/2004 | Lee et al. ..................... | 257/347 |

OTHER PUBLICATIONS

Katsunki Yanagiuchi, TDK Corporation, Saku, Nagano, Japan, "*Application Of Factor Analysis To Auger Electron Spectroscopy For Assessment Of CoSurface Fils On NiFe-Allow*", Proceedings of NAGANO magel '99, pp. 263-266.

* cited by examiner

*Primary Examiner*—David A Vanore
*Assistant Examiner*—Andrew Smyth
(74) *Attorney, Agent, or Firm*—Kenyon & Kenyon LLP

(57) ABSTRACT

A system and method for measuring the thickness of an ultra-thin multi-layer film on a substrate is disclosed. A physical model of an ultra-thin multilayer structure and Auger electron emission from the nano-multilayer structure is built. A mathematical model for the Auger Electron Spectroscopy (AES) measurement of the multilayer thin film thickness is derived according to the physical model. Auger electron spectroscopy (AES) is first performed on a series of calibration samples. The results are entered into the mathematical model to determine the parameters in the mathematical equation. The parameters may be calibrated by the correlation measurements of the alternate techniques. AES analysis is performed on the ultra-thin multi-layer film structure. The results are entered into the mathematical model and the thickness is calculated.

18 Claims, 5 Drawing Sheets

METHOD OF NANO THIN FILM THICKNESS MEASUREMENT BY AUGER ELECTRON SPECTROSCOPY

BACKGROUND INFORMATION

The present invention relates to thin-films on substrates. Specifically, the present invention relates to the use of Auger Electron Spectroscopy in the measurement of the thickness of an ultra-thin film on a substrate.

Ultra-thin films with thickness of less than five nanometers have found increasing application in the development of nano-technology. The exact thickness of such ultra-thin film is important for both the basic studies of multi-layer nano-structures and in the technical specifications of nano-device fabrication. For example, in the production of a magnetic head for a hard disc drive (HDD); an ultra-thin diamond-like-carbon (DLC) film is coated on the slider substrate, with an ultra-thin silicon (Si) film as the transition layer in between, to protect the writer/reader sensor. With the rapid increase of the HDD recording density to 80 G bits/inch$^2$, the flying height of the slider over the disc has been reduced to about 10 nm. Correspondingly, the thickness of DLC and Si layer must be reduced to 1.5 to 2.5 nm, and the accurate measurement of the ultra-thin film thickness becomes a key factor in the advanced giant magnetic resistance (GMR) head research and manufacturing. Several nano-metrology techniques, which can meet the above demand to some extent, exist in the prior art.

As shown in FIG. 1a, an Atomic Force Microscope (AFM) may test the thickness of an ultra-thin film 102 coated on a substrate 104 by scanning with an AFM tip 106 the depth of a photoresist-created groove 108 on the film 102. AFM has a resolution of 10 nm on the X-axis and Y-axis and a resolution of 0.1 nm on the Z-axis. The disadvantage of AFM is that it requires elaborate sample preparation and can only measure the thickness of a mono-layer or the combined total thickness of a multi-layer film. Therefore, the usefulness of AFM is limited to calibration applications.

As shown in FIG. 1b, a Transmission Electron Microscope (TEM) is a superior technique to measure an ultra-thin diamond-like carbon (DLC) layer thickness. A TEM is powerful in nano-scale dimension measurement, being able to directly observe and measure the ultra-thin film thickness at the one-millionth resolution, or even higher magnification with spatial resolution of about 0.1 nm. However, this method requires complicated and time-consuming sample preparation by a Focus Ion Beam (FIB), to create a cross section and, then, measuring the thickness by TEM. Such a "destructive" measurement is undesirable in many cases and not suitable for routing quality monitoring of a nano-device production.

Electron Spectroscopy for Chemical Analysis (ESCA) is a third known method for nano-thin film thickness measurement. ESCA is a non-destructive method used to measure the diamond-like carbon thickness on a silicon chip with an area resolution of approximately 1 mm, and in some cases up to 10 μm. As shown in FIG. 1c, the sample has a substrate 110 composed of $Al_2O_3TiC$ and is covered with a silicon layer 112 and a DLC layer 114. In this ESCA method, incident X-ray photon 116 causes the photoelectron emission at a specific angle (θ) from the surface of the DLC layer 114. Using the concentrations of silicon (Si %), aluminum (Al %), and carbon (C %) in the sample, calculated from the ESCA measured Si, AL, and C photoelectron signal intensities, the thickness of the DLC layer d 114 can be determined with the following equations:

$$d = \lambda \sin\theta \cdot \ln(1 + aR)$$

$$a = A \cdot \frac{BR'}{1 + BR'}, R' = \frac{Si\%}{Al\%}, R = \frac{C\% - J * Si\%}{Si\%}$$

$$A = \frac{I_{Si}^\infty}{I_C^\infty}, B = \frac{I_{Al}^\infty}{I_{Si}^\infty}$$

The variable a represents the intensity factor, the variables R and R' represent modification factors, the variable λ represents the attenuation length of a Si photoelectron passing by carbon layers, and J represents the ratio of SiC in Si layer. Using the same inputs, the thickness of the silicon layer d' 112 can be determined using the following equations:

$$d' = \lambda' \sin\theta \cdot \ln(1 + Br)$$

$$r = \frac{Si\%}{Al\%}$$

The variable r represents modification factors and the variable λ' represents the attenuation length of the Al photoelectron passing by the silicon layer. However, the area resolution of the ESCA method is normally in the millimeter range and about 10 μm at best. Therefore, this technique is not applicable to the thickness measurements of small area, such as down to the sub-micrometer, or even nanometer size, that is absolutely important for a submicro-device or nano-device research and manufacturing.

An Auger Electron Spectroscopy (AES) depth-profile method can be used to measure the relative thickness of an ultra-thin film. AES is an advanced solid surface analysis technique, based on the "Auger Effect". The Auger process is initiated with the removal of a core electron by an energetic primary electron beam, creating an ion with an inner shell vacancy. In the relaxation of the exited ion, an electron from a higher energy level fills the inner shell vacancy with the simultaneous emission of another higher level electron, called an "Auger Electron". The kinetic energy of the Auger electron is determined by the energy difference of the related 3 levels and is characteristic for the atom in which the Auger process occurs. An Auger electron spectrum plots the number of electrons detected as a function of electron kinetic energy. Elements are identified by the energy positions of the Auger peaks, while the concentration of an element is related to its Auger signal intensity. Furthermore, both theoretical and experimental research have shown that the mean free path of an Auger electron emission is less than 5 nm, meaning only a few to a dozen atomic layers can be detected by AES. AES is thus applied for the elementary composition analysis of a solid surface. AES and an Argon ion beam etching of the surface may be combined to perform a compositional depth profile analysis. Therefore, the thickness of a thin film can be obtained by taking account of the Argon ion sputtering time to remove the thin film layer, with the calibrated sputtering rate in hand. This method is also a destructive method and the accurate stuttering rate for a certain material is often difficult to obtain.

Lastly, an AES physical-mathematical model, for measuring the thickness of Cobalt thin film on a Nickel-Iron alloy substrate, has been reported. An example, as shown in FIG. 1d, includes a substrate 118 with a thin film 120 layer applied.

The substrate may be a nickel-iron alloy, with the thin film layer 120 made of cobalt. The angle 122 of an emission Auger electron 124 from normal is 43°. An AES physical-mathematics model method may be used to determine the thickness 126 of the thin film layer 120. The mathematics model is as follows:

$$t = \lambda_{Ni}^{Co} \cos\theta \ln\left(\frac{I_{Co}}{a * I_{NiFe}} + 1\right)$$

$$a = I_{Co}^{\infty} / I_{NiFe}^{\infty}$$

The variable $\lambda_{Ni}^{Co}$ represents the attenuation length of Auger electron of Ni element in substrate layer 118 through Co layer 120. This method applies only to a monolayer Cobalt film on a nickel-iron alloy substrate.

What is needed is a way to measure ultra-thin film ($\leq 5$ nm) layers of either single or double layers in an area of about 100 nm$^2$. For example, in the manufacturing of magnetic recording head, a key component device for computer Hard Disk Drive (HDD), the slider surface is coated with an ultra-thin film of diamond like carbon (DLC), with Si as the transition layer between DLC and $AL_2O_3$—TiC substrate. The flying height of a slider over a disk is currently down to about 10 nm. To control the thickness of the DLC and Si layer to between 2.5 nm and 1.5 nm becomes essential for the magnetic head production. Meanwhile, the key components of the slider, the writer and reader sensor are of a submicrometer or nanometer size, making the nano-metrology of the precise thickness measurement of the double layer ultra-thin film is vitally important for high-tech production. In addition, the measurement is supposed to be done without the need for a complicated sample preparation, or non-destructive and efficient enough to satisfy industrial testing.

DETAILED DESCRIPTION

A system and method for measuring the thickness of an ultra-thin multi-layer film structure on a substrate is disclosed. A physical model of an Auger emission from a nano multilayer structure is built. A mathematical model of Auger electron spectroscopy (AES) measurement of ultra-thin film thickness is derived according to the physical model. By performing the AES measurements on a series of calibration samples, the parameters in the mathematical model are determined. The parameters may be calibrated by comparing the results to the results from correlation measurement by alternative techniques, such as transmission electron microscope (TEM), atomic force microscope (AFM), and electron spectroscopy for chemical analysis (ESCA), establishing a physical model. AES analysis is performed on the practical samples to measure the signal intensity of the related elements in the ultra-thin multi-layer film structure. The results are input into the mathematical model and the thickness is calculated.

Figure 1A:
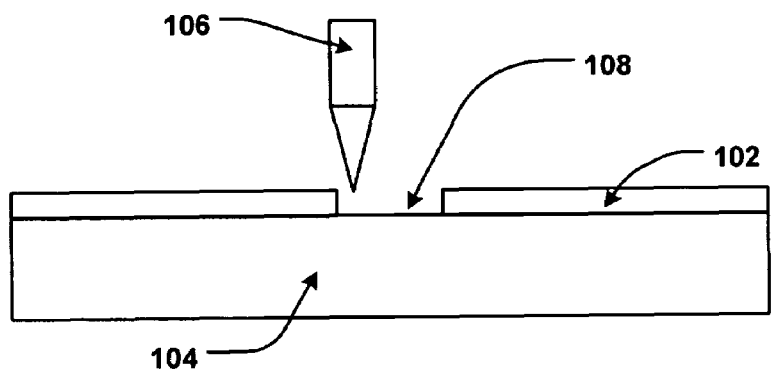
FIGS. 1a-d illustrate various methods for measuring thin film layers as known in the art.
Figure 1B:
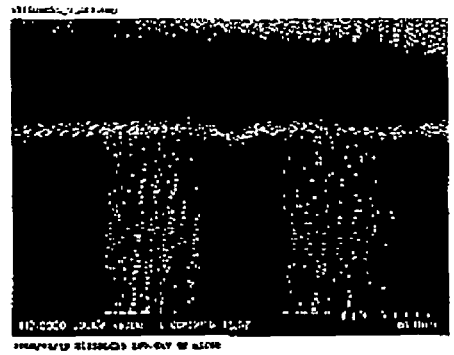
Figure 1C:
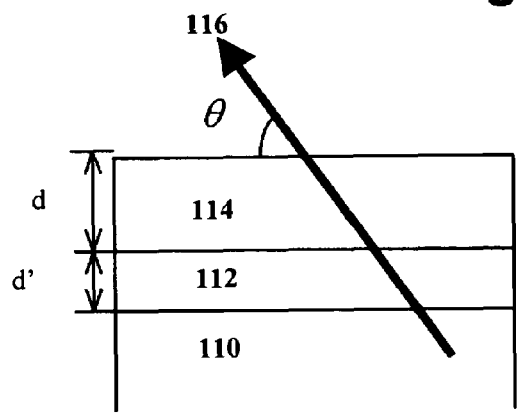
Figure 1D:
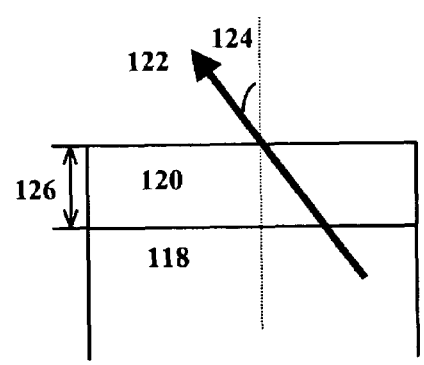
Figure 2:
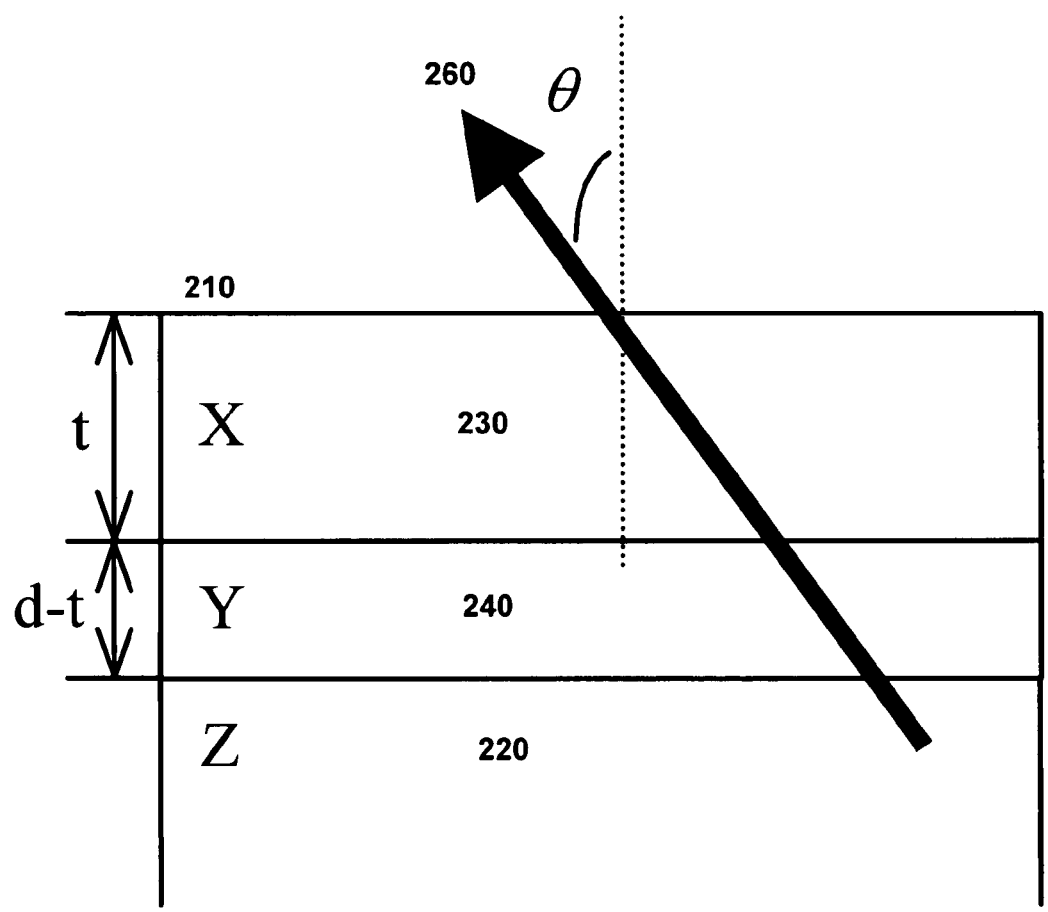
FIG. 2 illustrates the physical model according to the present invention.

FIG. 2 illustrates in a schematic diagram one embodiment of a physical model as practiced in the present invention. A physical model 210 of a substrate (Z) 220 with double-layer ultra-thin film is created. In one embodiment, the ultra-thin film layer has a first layer 230, or X layer, and a second layer 240, or Y layer. In one embodiment, the first layer 230 is a diamond like carbon (DLC) layer and the second layer 240 is a silicon layer placed on conductive ceramic layer made of $Al_2O_3TiC$ acting as a substrate 220.

Figure 3:
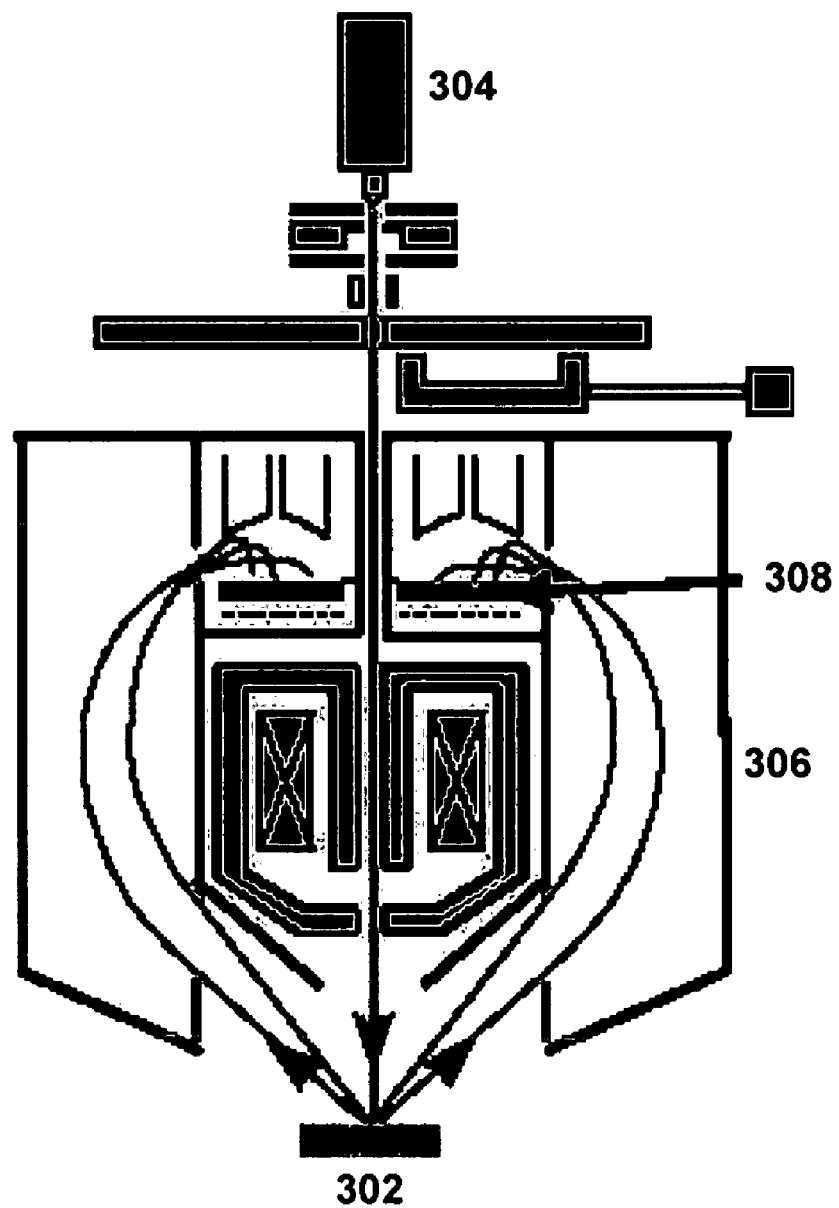
FIG. 3 illustrates one embodiment of an AES apparatus according to the present invention.

FIG. 3 illustrates in a block diagram one embodiment of an AES apparatus according to the present invention. The substrates 302 are loaded into a sampling holder, which allows multiple substrates to be tested in rapid succession. A field emission primary electron gun 304 fires an electron beam with a beam energy of between 1 and 20 keV and a beam size finely focused to about 10 nm, which guarantees the ultra-high spatial resolution for the sub-micro to nano-scale surface analysis. Auger electron is ejected from the surface of the multi-layer substrates by the incident primary electron and, then, guided into and energy analyzed by an electron energy analyzer, such as a cylinder mirror analyzer (CMA) 306. The Auger electron passes through the CMA 306 and is collected at an Auger electron multi-channel detector 308. The electron detector 308 will amplify the signal from the electron multiplier before forwarding it to an online computer. The online computer acts as a x-y recorder or oscilloscope to measure the signal intensities in order to perform a multi-layer ultra-thin film thickness calculation, with a mathematical model derived from the physical model. In one embodiment, the tests are first performed on a series of calibration samples, prepared according to the physical model of the multilayer, ultra-thin film structure, to determine the parameters in the mathematical model.

In a further embodiment, the parameters are calibrated by comparing the results to the results obtained by using an atomic force microscope (AFM), a transmission electron microscope (TEM), and/or electron spectroscopy for chemical analysis (ESCA). Table I shows an example of the resulting comparisons.

TABLE 1

| The parameters calibrated by AFM and ESCA data | | | | |
|---|---|---|---|---|
| Intensity Ratio | ABS (Al2) | Ni—Fe (Ni1) | Ni—Fe—Co (Co1) | Lead (Au3) |
| a' | 0.946 | 2.319 | 2.043 | 5.529 |
| a" | 1.090 | 1.011 | 1.011 | 1.011 |

| Modification Factor | ABS (Al2) | Ni—Fe (Ni1) | Ni—Fe—Co (Co1) | Lead (Au3) |
|---|---|---|---|---|
| R | 1.000 | 1.420 | 1.420 | 1.652 |
| R' | 1.000 | 1.263 | 1.263 | 0.937 |

| Mean Free Path | ABS (Al2) | Ni—Fe (Ni1) | Ni—Fe—Co (Co1) | Lead (Au3) |
|---|---|---|---|---|
| $\lambda_{Si}^{DLC}$ | 3.100 nm | 3.1 nm | 3.1 nm | 3.1 nm |
| $\lambda_{Substrate}^{Si}$ | 2.400 nm | 1.951 nm | 1.951 nm | 1.260 nm |

After the parameters have been determined, they and the mathematical model are inputted into the software installed into the online computer 322 of the AES. The ultra-thin film thickness can be calculated by the experimentally obtained Auger signal intensity of substrate, the first and the second layer material, respectively.

According to the physical model shown in FIG. 2, the mathematical model of the AES measurement of a double-layer thin film on a substrate may be derived in the following method:

For the homogeneous, $I_A = \int_1^\infty g_A C_A e^{-\frac{x}{\lambda_A \cos\theta}} \partial x$, $g_A = T(E)D(E)I_o \sigma_A \gamma_A (1 + r_M)$

⇓

$I_A^\infty = g_A C_A \lambda_A^A \cos\theta$

⇓

For the Z substrate, $I_X^X = g_X C_X \int_0^1 e^{-\frac{x}{\lambda_X^X \cos\theta}} \partial x$, $I_Y^X = g_Y C_Y \int_1^d e^{-\frac{(x-t)}{\lambda_Y^Y \cos\theta}} \cdot e^{-\frac{t}{\lambda_Y^X \cos\theta}} \partial x$, $I_Z^X = g_Z C_Z \int_d^\infty e^{-\frac{t}{\lambda_Z^X \cos\theta}} \cdot e^{-\frac{(d-t)}{\lambda_Z^Y \cos\theta}} \cdot e^{-\frac{(x-d)}{\lambda_Z^Z \cos\theta}} \partial x$

⇓

$I_X^X = I_X^\infty \cdot \left(1 - e^{-\frac{t}{\lambda_X^X \cos\theta}}\right)$, $I_Y^Z = I_Y^\infty \cdot e^{-\frac{t}{\lambda_Y^X \cos\theta}} \left[1 - e^{-\frac{(d-t)}{\lambda_Y^Y \cos\theta}}\right]$, $I_Z^X \approx I_Z^\infty \cdot e^{-\frac{t}{\lambda_Z^X \cos\theta}} \cdot e^{-\frac{(d-t)}{\lambda_Z^Y \cos\theta}}$ ⇓ $\lambda_X^X = \lambda_Y^X, \lambda_X^Y = \lambda_Y^Y$

⇓

$I_X^X = I_X^\infty \cdot \left(1 - e^{-\frac{t}{\lambda_Y^X \cos\theta}}\right)$, $I_Y^X = I_Y^\infty \cdot e^{-\frac{t}{\lambda_Y^X \cos\theta}} \left(1 - e^{-\frac{(d-t)}{\lambda_Z^Y \cos\theta}}\right)$, $I_Z^X = I_Z^\infty \cdot e^{-\frac{(d-t)}{\lambda_Z^Y \cos\theta}} \cdot e^{-\frac{t}{\lambda_Z^X \cos\theta}}$

⇓

By $\frac{I_Y^X}{I_Z^X}$, If $a' = \frac{I_Z^\infty}{I_Y^\infty}$, $R' = \frac{I_Y^X}{I_Z^X}$, then $(d - t) = \lambda_Z^Y \cos\theta \ln(a' \cdot R' + 1)$ By $\frac{I_X^X}{I_Y^X}$, If $a = \frac{I_Y^\infty}{I_X^\infty} \cdot \left(1 - e^{-\frac{(d-t)}{\lambda_Z^Y \cos\theta}}\right)$, $R = \frac{I_X^X}{I_Y^X}$, then $t = \lambda_Y^X \cos\theta \cdot \ln(a \cdot R + 1)$ If $a'' = \frac{I_Y^\infty}{I_Y^\infty}$, then $a = a'' \cdot \frac{a' R'}{1 + a' R'}$ In the above derivation, the variable "$C_A$" represents concentration of element A. The variable "$\lambda_A$" represents the attenuation length of Auger electron. The variable "θ" represents emission angle between the surface normal and the detector direction. The variable "$\sigma_A$" represents a cross section of Auger process. The variable "T(E)" represents transmission factor, a function of kinetic energy E of the Auger electron. The variable "D(E)" represents the detection efficiency of the electron multiplier, a factor that may vary with time. The variable "$r_M$" represents an electron backscatter factor that is matrix dependent. The variable "$I_o$" represents the primary current.

Figure 4:
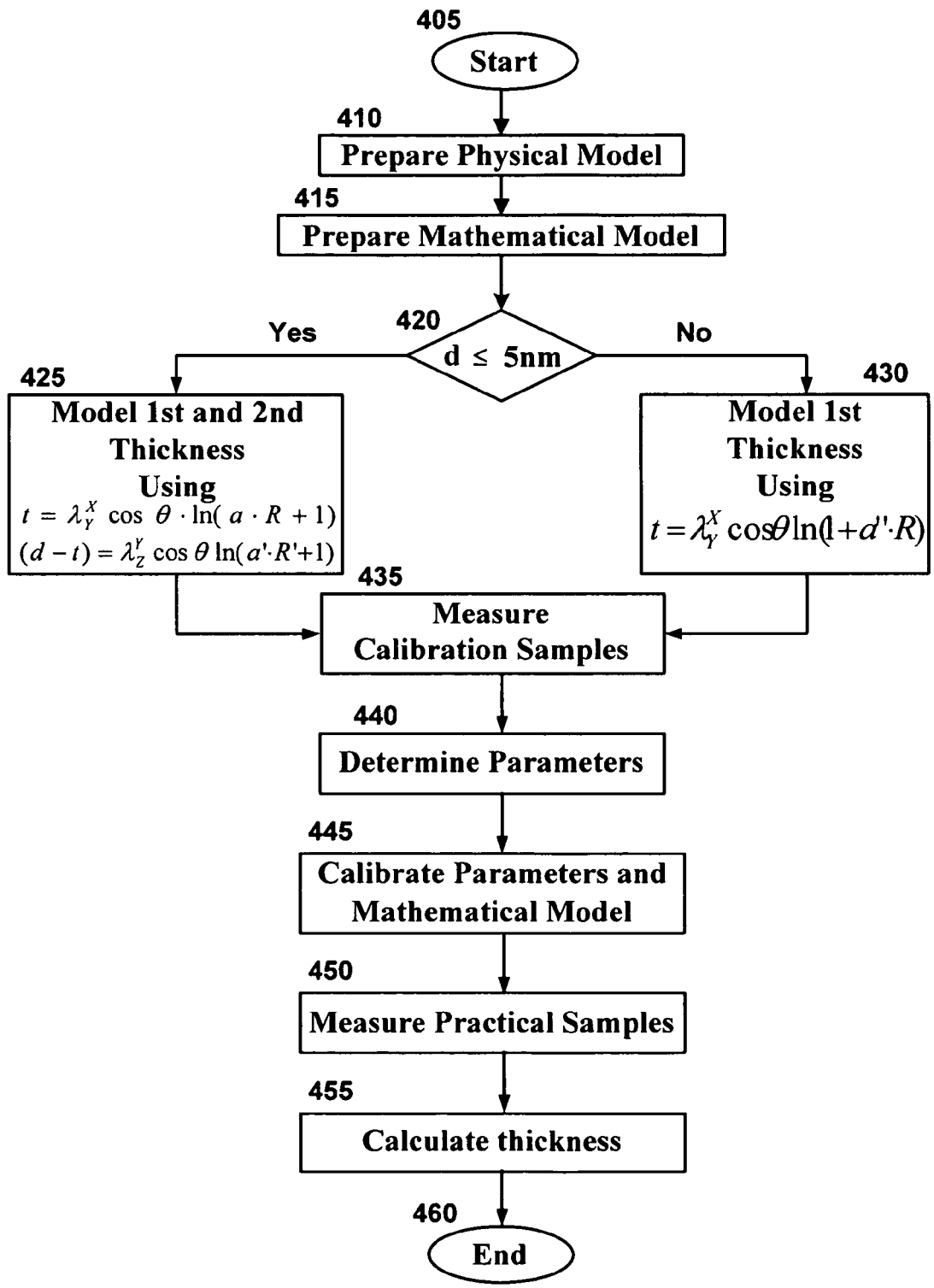
FIG. 4 illustrates in a flowchart one embodiment of a method for measuring thin film layers.

FIG. 4 illustrates in a flowchart one embodiment of a method for determining ultra-thin film thickness according to the present invention. The process starts (Block 405) by designing a physical model of the ultra-thin, multi-layer film structure (Block 410). Then, a mathematical model for calculating the thickness of the ultra-thin, multi-layer film structure is derived based on the structure of the physical model (Block 415). If the thickness (d) of the ultra-thin, multi-layer film structure is greater than 5 nanometers (Block 420), the thickness (t) of the first layer is modeled using the following equation (Block 425):

$t = \lambda_Y^X \cos\theta \ln(l + a'' \cdot R)$.

If the thickness (d) of the ultra-thin, multi-layer film structure is less than or equal to 5 nanometers (Block 420), the thickness (t) of the first layer is modeled using the following equation:

$t = \lambda_Y^X \cos\theta \cdot \ln(a \cdot R + 1)$ and the thickness (d−t) of the second layer is modeled using the following equation (Block 430):

$(d - t) = \lambda_Z^Y \cos\theta \ln(a' \cdot R' + 1)$.

An AES measurement is performed on a series of calibration samples to measure the signal intensities of the related elements in a multilayer structure of known-thickness (Block 435). Then, the acquired data is input into the mathematical model to determine all the parameters in the mathematical equation (Block 440). The parameters are calibrated by comparing the calculated thickness with the results provided by TEM, AFM, and ESCA (Block 445). Once all the proper parameters are determined and calibrated, the physical-mathematical model may be considered established. An AES measurement may then be performed on the practical samples of the ultra-thin film structure (Block 450). The thickness is calculated using the mathematical model (Block 455), finishing the process (Block 460).

This measurement technique may be applied in the data storage industry, such as in the mass production of hard disk drives (HDD), GMR head manufacturing, head quality routine monitoring, failure analysis, research and development, and others.

Figure 5:
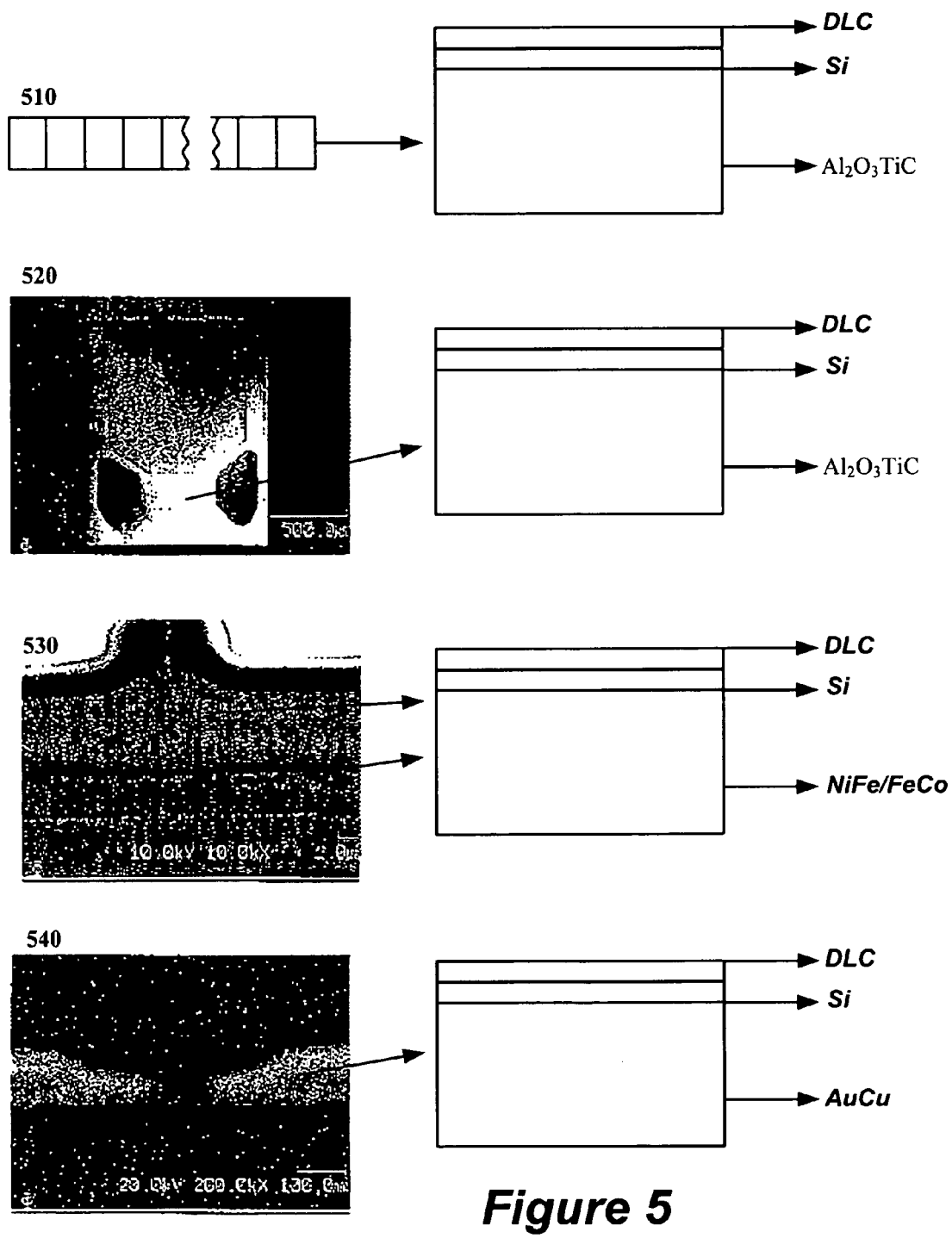
FIG. 5 illustrates in a block diagram the positioning of four different areas of measurement.

In one embodiment, the nano metrology method is applied in the measurement of the thickness of ultra-thin DLC and Si coating layers on the GMR head of the HDD. FIG. 5 illustrates in a block diagram the positioning of four different areas of measurement. Mass produced rowbars 510, usually sized at 1×40 mm, are cut from the magnetic recording wafer and coated with ultra-thin DLC. Silicon acts as the transition layer between DLC and the substrate material, $Al_2O_3$—TiC, to protect the pole area (writer/reader sensor). Then, the air-bearing surface (ABS) 520 is created by photolithography on each slider (1×1 mm). AES, ESCA, AFM and TEM are applied to measure the DLC and Si thickness. The target thickness of the DLC/Si layers are ranged from 1.5 nm to 4.0 nm, respectively. The results of DLC and Si thickness measurements on the substrate of $Al_2O_3TiC$ (rowbar, sized in 1×40 mm) and ABS of slider (0.2-0.5 mm), a Ni—Fe alloy 530 (shield of writer and reader sensor, 1-5 μm), and on a substrate of Au/Cu 540 (lead material, 40 nm) are listed in the table 2.

TABLE 2

The comparison of AES, ESCA, AFM and TEM data

| | Measured Area | | | | | | | | | | | |
|---|---|---|---|---|---|---|---|---|---|---|---|---|
| | Rowbar (without ABS) | | | ABS on Slider/Rowbar | | | Shield | | | Lead | | |
| method | DLC | Si | Total | DLC | Si | Total | DLC | Si | Total | DLC | Si | Total |
| Target (Å) | 25 | 10 | 35 | 25 | 10 | 35 | 25 | 10 | 35 | 25 | 10 | 35 |
| AES data (Å) | 24.7 | 30.6 | 55.3 | 24.7 | 30.6 | 55.3 | 29.8 | 30 | 59.8 | 28.6 | 32.7 | 61.3 |
| ESCA data (Å) | 29.2 | 25.7 | 54.9 | — | — | — | — | — | — | — | — | — |
| AFM data (Å) | — | — | 57.9 | — | — | 57.9 | — | — | 57.9 | — | — | 57.9 |
| TEM data (Å) | — | — | 60 | — | — | 60 | — | — | 60 | — | — | 60 |
| Target (Å) | 10 | 25 | 35 | 10 | 25 | 35 | 10 | 25 | 35 | 10 | 25 | 35 |
| AES data (Å) | 15 | 35.6 | 50.6 | 15 | 35.6 | 50.6 | 12.6 | 40.8 | 53.4 | 14.8 | 40.4 | 53.2 |
| ESCA data (Å) | 11.9 | 37.2 | 49.1 | — | — | — | — | — | — | — | — | — |
| AFM data (Å) | — | — | 50.5 | — | — | 50.5 | — | — | 50.5 | — | — | 50.5 |
| TEM data (Å) | — | — | 48 | — | — | 48 | — | — | 48 | — | — | 48 |
| Target (Å) | 40 | 25 | 65 | 40 | 25 | 65 | 40 | 25 | 65 | 40 | 25 | 65 |
| AES data (Å) | 48.9 | — | — | 48.9 | — | — | 47.4 | — | — | 44.6 | — | — |
| ESCA data (Å) | 37.3 | 44.2 | 81.5 | — | — | — | — | — | — | — | — | — |
| AFM data (Å) | — | — | 82.2 | — | — | 82.2 | — | — | 82.2 | — | — | 82.2 |
| TEM data (Å) | — | — | 78 | — | — | 78 | — | — | 78 | — | — | 78 |
| Target (Å) | 25 | 40 | 65 | 25 | 40 | 65 | 25 | 40 | 65 | 25 | 40 | 65 |
| AES data (Å) | 49.5 | — | — | 49.5 | — | — | 47.5 | — | — | 50 | — | — |
| ESCA data (Å) | 28.2 | 50.8 | 79 | — | — | — | — | — | — | — | — | — |
| AFM data (Å) | — | — | 83.7 | — | — | 83.7 | — | — | 83.7 | — | — | 83.7 |
| TEM data (Å) | — | — | 84 | — | — | 84 | — | — | 84 | — | — | 84 |

TEM and AFM are applied as the calibration measurement as they need complicated sample preparation and are the destructive methods. AES and ESCA are the non-destructive methods and do not need complicated sample preparation. However, due to the poor spatial resolution, ESCA can only measure the DLC/Si thickness on the rowbar without ABS. In contrary, AES is the only method, which has the all advantages of non-destructive, non-complicated sample preparation, efficient and can measure all the area, including rowbar, ABS of slider, pole area, and even the nano area of the GMR sensor and the lead.

What is claimed is:

1. A thickness measurement method, comprising:
    performing an Auger electron spectroscopy analysis on a thin film layer on a substrate;
    collecting a set of auger electron spectroscopy data of the thin film layer;
    performing a calculation on the set of data using a predetermined mathematical model; and
    determining a thickness of the thin film layer based on the calculation, wherein at least a first thin film layer and a second thin film layer having a combined thickness are applied to the substrate.

2. The thickness measurement method of claim 1, wherein both thin film layers are ultra-thin film layers of less than or equal to 5 nanometers combined.

3. The thickness measurement method of claim 2, further comprising:
    determining a thickness of the first film layer (t) by using an attenuation length between the first thin-film layer (X) and the second thin-film layer (Y) ($\lambda$), an Auger electron path angle from normal ($\theta$), a first intensity ratio (a) and a first modification factor (R), in a mathematical model as follows:

$t = \lambda_Y^X \cos\theta \cdot \ln(a \cdot R + 1)$; and determining a thickness of the first film layer (d-t) by using an attenuation length between the second thin-film layer (X) and the substrate (Y) ($\lambda$), an Auger electron path angle from normal ($\theta$), a second intensity ratio (a') and a second modification factor (R'), in a mathematical model as follows:

$(d-t) = \lambda_Z^Y \cos\theta \ln(a' \cdot R' + 1)$.

4. The thickness measurement method of claim 1, further comprising determining a thickness of the first film layer (t) by using an attenuation length between the first thin-film layer (X) and the second thin-film layer (Y) ($\lambda$), an Auger electron path angle from normal ($\theta$), an intensity ratio (a") and a modification factor (R), in a mathematical model as follows:

$t = \lambda_Y^X \cos\theta \ln(1 + a'' \cdot R)$.

5. The thickness measuring method of claim 1, further comprising:
    building a physical model of the thin film layer on the substrate;
    deriving a mathematical model of Auger electron emission from the thin film layer on the substrate;
    determining values for a set of parameters for the mathematical model using Auger electron spectroscopy; and
    calibrating the set of parameters by correlation measurements using alternate techniques.

6. The thickness measurement method of claim 5, wherein the alternate measurement techniques are from a group consisting of an atomic force microscope, a transmission electron microscope, and electron spectroscopy for chemical analysis.

7. The thickness measurement method of claim 5, further comprising altering the predetermined mathematical model for different physical models.

8. A set of instructions residing in a storage medium, said set of instructions capable of being executed by a processor to implement a method for processing data, the method comprising:
- performing an Auger electron spectroscopy on a thin film layer on a substrate;
- collecting a set of data from the auger electron spectroscopy of the thin film layer;
- performing a calculation on the set of data using a predetermined mathematical model; and
- determining a thickness of the thin film layer based on the calculation, wherein at least a first thin film layer and a second thin film layer having a combined thickness are applied to the substrate.

9. The set of instructions of claim 8, wherein both thin film layers are ultra-thin film layers of less than or equal to 5 nanometers combined.

10. The set of instructions of claim 9, further comprising:
- determining a thickness of the first film layer (t) by using an attenuation length between the first thin-film layer (X) and the second thin-film layer (Y) ($\lambda$), an Auger electron path angle from normal ($\theta$), a first intensity ratio (a) and a first modification factor (R), in a mathematical model as follows:

$$t = \lambda_Y^X \cos\theta \cdot \ln(a \cdot R + 1); \text{ and}$$

- determining a thickness of the first film layer (d-t) by using an attenuation length between the second thin-film layer (X) and the substrate (Y) ($\lambda$), an Auger electron path angle from normal ($\theta$), a second intensity ratio (a') and a second modification factor (R'), in a mathematical model as follows:

$$(d-t) = \lambda_Z^Y \cos\theta \, \ln(a' \cdot R' + 1).$$

11. The set of instructions of claim 8, farther comprising determining a thickness of the first film layer (t) by using an attenuation length between the first thin-film layer (X) and the second thin-film layer (Y) ($\lambda$), an Auger electron path angle from normal ($\theta$), an intensity ratio (a'') and a modification factor (R), in a mathematical model as follows:

$$t = \lambda_Y^X \cos\theta \, \ln(1 + a'' \cdot R).$$

12. The set of instructions of claim 8, further comprising:
- determining values for a set of parameters for the predetermined mathematical model using Auger electron spectroscopy on a physical model of the thin film layer on the substrate; and
- calibrating the set of parameters using alternate measurement techniques.

13. The set of instructions of claim 12, wherein the alternate measurement techniques are from a group consisting of an atomic force microscope, a transmission electron microscope, and electron spectroscopy for chemical analysis.

14. The set of instructions of claim 12, further comprising altering the predetermined mathematical model for different physical models.

15. A testing system, comprising:
- an Auger electron spectroscopy device to perform an analysis on a first thin film layer and a second thin film layer on a substrate; and
- a computer to collect a set of data from the auger electron spectroscopy of the thin film layer and to perform a calculation on the set of data using a predetermined mathematical model to determine a thickness of the thin film layer based on the calculation.

16. The thickness measuring system of claim 15, wherein both thin film layers are ultra-thin film layers of less than or equal to 5 nanometers combined.

17. The thickness measuring system of claim 16, wherein the computer determines a thickness of the first film layer (t) by using an attenuation length between the first thin-film layer (X) and the second thin-film layer (Y) ($\lambda$), an Auger electron path angle from normal ($\theta$), a first intensity ratio (a) and a first modification factor (R), in a mathematical model as follows:

$$t = \lambda_Y^X \cos\theta \cdot \ln(a \cdot R + 1); \text{ and}$$

- determines a thickness of the first film layer (d-t) by using an attenuation length between the second thin-film layer (X) and the substrate (Y) ($\lambda$), an Auger electron path angle from normal ($\theta$), a second intensity ratio (a') and a second modification factor (R'), in a mathematical model as follows:

$$(d-t) = \lambda_Z^Y \cos\theta \, \ln(a' \cdot R' + 1).$$

18. The thickness measuring system of claim 16, further comprising determining a thickness of the first film layer (t) by using an attenuation length between the first thin-film layer (X) and the second thin-film layer (Y) ($\lambda$), an Auger electron path angle from normal ($\theta$), an intensity ratio (a'') and a modification factor (R), in a mathematical model as follows:

$$t = \lambda_Y^X \cos\theta \, \ln(1 + a'' \cdot R).$$

* * * * *

UNITED STATES PATENT AND TRADEMARK OFFICE
CERTIFICATE OF CORRECTION

PATENT NO. : 7,582,868 B2  Page 1 of 1
APPLICATION NO. : 11/192199
DATED : September 1, 2009
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this

Fourteenth Day of September, 2010

David J. Kappos
*Director of the United States Patent and Trademark Office*